(12) United States Patent
Ideker et al.

(10) Patent No.: US 6,243,603 B1
(45) Date of Patent: Jun. 5, 2001

(54) METHODS AND APPARATUS FOR DETECTING MEDICAL CONDITIONS OF THE HEART

(75) Inventors: Raymond E. Ideker, Birmingham, AL (US); Bruce H. KenKnight, Maple Grove, MN (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/153,407

(22) Filed: Sep. 15, 1998

(51) Int. Cl.⁷ ...................................................... A61N 1/39
(52) U.S. Cl. ..................................................... 607/5; 607/9
(58) Field of Search .................................. 607/4, 5, 9, 14

(56) References Cited

U.S. PATENT DOCUMENTS

| | | | | |
|---|---|---|---|---|
| 4,928,688 | * | 5/1990 | Mower | 607/9 |
| 5,514,161 | * | 5/1996 | Limousin | 607/9 |
| 5,720,768 | * | 2/1998 | Verboven-Nelissen | 607/9 |

* cited by examiner

Primary Examiner—George R. Evanisko
(74) Attorney, Agent, or Firm—Myers Bigel Sibley & Sajovec

(57) ABSTRACT

An implantable system for detecting electrical activity from a patient's heart comprises a first sensing electrode configured for positioning through the coronary sinus ostium and within a vein on the left surface of the left ventricle of the heart for sensing electrical activity from the heart, and a detector operatively associated with the first sensing electrode for determining (e.g., diagnosing or prognosing) a medical condition of the heart with the sensed electrical activity. Typically the system further comprises a second sensing electrode configured for positioning in the right ventricle of the heart, where the detector is operatively associated with both the first sensing electrode and the second sensing electrode. The second sensing electrode may be positioned in other locations as well, such as also within a vein on the left surface of the left ventricle of the heart (although spaced apart from the first sensing electrode), in the right atrium, in the superior vena cava, etc. Finally, a third sensing electrode may also be included, with the third electrode positioned in any of the foregoing locations (again, spaced apart from the first and second electrodes), with the detector operatively associated with all of the first, second, and third sensing electrodes. Determination of a medical condition may be carried out by any suitable means, such as by detecting premature beats in the heart. The method is particularly useful for identifying the chamber of premature beat origin.

28 Claims, 5 Drawing Sheets

METHODS AND APPARATUS FOR DETECTING MEDICAL CONDITIONS OF THE HEART

FIELD OF THE INVENTION

This invention concerns an implantable device that can be incorporated into a cardioverter/defibrillator for determining various medical conditions of the heart, particularly various types of arrhythmias or cardiac ischemia. The device may be used to diagnose current conditions or predict future conditions.

BACKGROUND OF THE INVENTION

At this time, brief application of an electric shock to the heart muscle is the only viable method that has been shown to be an effective treatment for termination of the most lethal ventricular tachyarrhythmia, ventricular fibrillation. Recently, implantable rhythm management systems have been developed to automatically monitor the heart rhythm and deliver appropriate electrical therapy when the heart beat is too fast or too slow. When a bradyarrhythmia is detected, the device issues low voltage (~5 V) electrical stimuli to drive the heart at a slightly faster rate. When a tachyarrhythmia is detected, the device charges one or more capacitors to ~700 V and then discharges the capacitors when the tachyarrhythmia condition is reconfirmed by the device. Such rhythm management systems are called implantable cardioverter defibrillators (ICDs).

The lead systems commonly connected to ICDs have a sensing and pacing electrode located at the tip of the lead located in the right ventricular apex and in the right atrium. Some but not all lead systems have another electrode in the superior vena cava. Contemporary ICDs utilize the metallic shell (or case) of the ICD as an electrode that is active during defibrillation shocks. Such an arrangement permits defibrillation with lower strength shocks since the electrical resistance during the shock is lower with the shell electrode compared to electrode configurations without the shell electrode. Typically, the superior vena cava electrode and the shell electrode are made electrically common. In this case, the electrode configuration is said to be RV→SVC+Shell. Often the shell electrode is referred to as the "can" electrode, since the ICD case is typically referred to by those skilled in the art as the "can."

U.S. Pat. No. 5,282,837 to Adams et al. describes, in FIG. 1 and accompanying text, an atrial defibrillator and method in which a lead 36 is inserted into the coronary sinus so that a first tip electrode 42 is within the coronary sinus adjacent the left ventricle, a second ring electrode 44 is within the coronary sinus beneath the left atrium, and the third electrode 46 within the right atrium or superior vena cava. The first electrode serves as a sensing electrode, the second electrode (still in the coronary sinus) serves as both a sensing and defibrillating electrode, and the third electrode serves as a sensing and defibrillating electrode (see Col. 5 line 57 to Col. 6 line 12).

U.S. Pat. No. 5,433,729 to Adams et al. describes, in FIG. 9 and accompanying text, a lead system 250 configured in accordance with that described above. A first (right ventricle) lead 252 includes an elongate large surface area electrode 256, a distal or tip sense electrode 258, and a ring or proximal sense electrode 260. Sense electrodes 258, 260 are positioned in and in contact with the wall of the right ventricle, and elongate electrode 256 is in the right atrium. A second (coronary sinus) lead 254 includes a tip, or distal sense electrode 264, a ring or proximal sense electrode 266, and a second elongate, large surface area electrode 262. Distal and proximal sense electrodes 264, 266 are both adjacent the left ventricle within the great vein, and elongate electrode 262 is within the coronary sinus beneath the left atrium. The right ventricle sense electrodes 258, 260 are coupled to inputs 50a, 50b of first sense amplifier 50; the great vein sense electrodes 264, 266 are coupled to inputs 52a, 52b of second sense amplifier 52. This is to provide sensing of the right ventricle and the left ventricle, and the non-coincident sensing of the depolarization activation waves. for synchronizing delivery of energy to the atria (see column 15 line 34 to column 16 line 54; column 5 lines 62–64).

U.S. Pat. No. 5,014,696 to Mehra describes an endocardial defibrillation electrode system in which a coronary sinus electrode extending from an area adjacent the opening of the coronary sinus and terminating in the great vein is used in combination with subcutaneous plate electrodes and with right ventricular electrodes. The coronary sinus electrode 78 encircles the left ventricle cavity 86 (Col. 5 lines 50–51; FIG. 5B). It is stated "it is important not to extend the electrode 78 downward through the great vein 80 toward the apex 79 of the heart" (col. 5 lines 28–30). U.S. Pat. No. 5,165,403 to Mehra (Medtronic, Inc.) describes an atrial defibrillation electrode 112 that is located "within the coronary sinus and the great cardiac vein."

U.S. Pat. No. 5,099,838 to Bardy describes a defibrillation electrode in the great vein that is used in combination with subcutaneous plate electrodes and with right ventricular electrodes (col. 1 line 65 to col. 2 line 2). With respect to the great vein electrode, it is stated at column 5, lines 20–33 therein: "When so mounted, the elongate defibrillation electrode 78 extends from a point adjacent the opening of the coronary sinus 74 and into the great vein 80. This provides a large surface area defibrillation electrode which is generally well spaced from the ventricular defibrillation electrode 74 and provides good current distribution in the area of the left ventricle 77. It is desireable to extend the electrode 78 around the heart as far as possible. However, it is important not to extend the electrode 78 downward through the great vein 80 toward the apex 79 of the heart, as this will bring the coronary sinus and right ventricular electrodes into close proximity to one another, interfering with proper current distribution. U.S. Pat. No. 5,193,535 to Bardy (filed Aug. 27, 1991) also describes a great vein electrode. At column 7, lines 31–35, it is stated: "The coronary sinus lead is provided with an elongated electrode located in the coronary sinus and great vein region at 112, extending around the heart until approximately the point at which the great vein turns downward toward the apex of the heart."

U.S. Pat. No. 5,431,683 to Bowald et al. describes a ventricular defibrillation electrode system in which an electrode is placed through the coronary sinus into a peripheral vein of the heart. The term "peripheral vein" is defined therein as to encompass "the venous side of the coronary vessels running between the base and the apex of the heart. The veins include the middle and small cardiac veins, and the portion of the great cardiac vein which runs between the base and apex of the heart. The definition of peripheral veins' used herein therefore excludes that portion of the great cardiac vein which runs along the base plane of the heart, which has been used [as] a site for electrode placement in prior art electrode systems." The electrodes are in the shape of a helix to apply pressure against the inner wall (col. 4, lines 14–17), with blood being able to flow unobstructed through the interior of the helix (column 4, lines 46–48). See also U.S. Pat. No. 5,423,865 to Bowald.

U.S. Pat. No. 5,690,686 to Min et al. describes an atrial defibrillation method in which a coronary sinus/great vein electrode is coupled to a right atrial/superior vena cava electrode and a subcutaneous electrode in the form of the housing of an implantable defibrillator. The device is stated to be preferably practiced as a combined atrial/ventricular defibrillator (col. 2, lines 26–35).

When ICDs are implanted in patients, physicians perform arrhythmia conversion testing to assure that the clinical arrhythmias can be successfully aborted by the device. In a typical clinical implant, ventricular fibrillation is electrically induced by the physician, and the ICD system is commanded to deliver a test shock of known strength after waiting about 10 seconds. If the test shock is successful, the strength is systematically reduced during subsequent trials until a strength that fails to convert the tachyarrhythmia is identified. The immediately prior shock strength that successfully converted the tachyarrhythmia is commonly referred to as the defibrillation threshold (DFT). DFTs vary among patients. The object of DFT testing at ICD implant is to identify patients that are likely not to benefit from the ICD (DFT is too high relative to maximum device output to confer a safe margin).

Technological advances have resulted in rapid evolution of ICD systems. One of the most pronounced differences in contemporary ICD systems and previous ICD systems is the reduced size of the pulse generator. Further reductions in device size may require reducing the peak voltage delivered by the device. However, to assure that nearly all patients in the ICD patient population will have DFTs lower than the maximum output, future devices will need to provide shock delivery means that substantially reduce the DFT.

SUMMARY OF THE INVENTION

A first aspect of the present invention is an implantable system for detecting electrical activity from a patient's heart. The system comprises a first sensing electrode configured for positioning through the coronary sinus ostium and within a vein on the left surface of the left ventricle of the heart for sensing electrical activity from the heart, and a detector operatively associated with the first sensing electrode for determining (e.g., diagnosing or prognosing) a medical condition of the heart with the sensed electrical activity. Typically the system further comprises a second sensing electrode configured for positioning in the right ventricle of the heart, where the detector is operatively associated with both the first sensing electrode and the second sensing electrode. The second sensing electrode may be positioned in other locations as well, such as also within a vein on the left surface of the left ventricle of the heart (although spaced apart from the first sensing electrode), in the right atrium, in the superior vena cava, etc. Finally, a third sensing electrode may also be included, with the third electrode positioned in any of the foregoing locations (again, spaced apart from the first and second electrodes), with the detector operatively associated with all of the first, second, and third sensing electrodes. Determination of a medical condition may be carried out by any suitable means, such as by detecting premature beats in the heart. The method of the present invention is particularly useful for identifying the chamber of premature beat origin (e.g., left ventricle, right ventricle, left atrium, or right atrium).

The detector may be configured to detect the presence of sinus rhythm with syntactic relationships among electrogram features. The detector may be configured to predict cardiac arrhythmia in the patient prior to the onset of the cardiac arrhythmia, or the present occurence of cardiac arrhythmia in the patient. The detector may be configured to discriminate the location of origin of premature beats in the heart (e.g., to discriminate an atrial location of origin from a ventricular location of origin of premature beats in the heart, with or without the ability to discriminate left ventricular from right ventricular locations of origin, and with or without the ability to discriminate left atrial from right atrial locations of origin).

Also disclosed is a method for detecting cardiac ischemia in a patient. The method comprises detecting electrical activity from the heart of the patient from a first sensing electrode positioned within a vein on the left surface of the left ventricle of the heart; detecting electrical activity from the heart of the patient from a second sensing electrode positioned within the right ventricle of the heart; and determining the occurrence of cardiac ischemia from the detected electrical activity. The determining step may be carried out by detecting the occurence of premature beats in the heart.

Also disclosed is a method of selecting a cardiac therapy to be delivered to a patient's heart by an implantable cardioverter/defibrillator system. The method comprises detecting a first set of electrical activity from the heart from a first sensing electrode positioned within a vein on the surface of the left ventricle of the heart; detecting a second set of electrical activity from the heart from a second sensing electrode positioned within the right ventricle of the heart; then selecting an electrical therapy to be delivered by the implantable system based on the first and second sets of detected electrical activity; and then delivering the selected electrical therapy.

In particular embodiments of the invention, a therapy circuit may be provided so that the detected medical condition initiates a therapeutic pulse to the heart to correct or prevent the detected or predicted medical condition.

The foregoing and other objects and aspects of the present invention are explained in detail in the drawings herein and the specification set forth below.

DETAILED DESCRIPTION OF THE PREFERRED EMBODIMENTS

Figure 1:
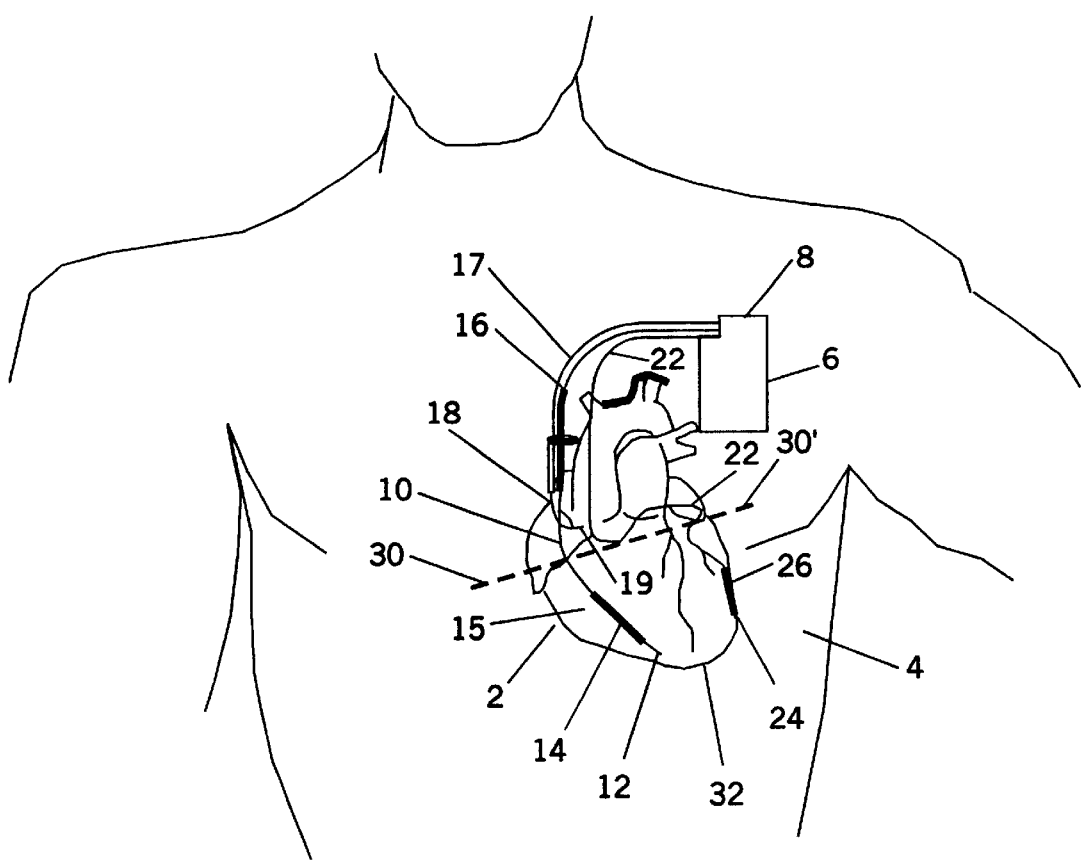
FIG. 1 illustrates an apparatus of the present invention, as implanted in the left pectoral region of a human subject and with electrodes positioned in the subject's heart.

An implantable cardioverter/defibrillator (ICD) of the present invention includes an implantable housing that contains a hermetically sealed electronic circuit. The housing optionally, but preferably, includes an electrode comprising an active external portion of the housing, with the housing implanted in the left or right, preferably left, thoracic region of the patient (e.g., subcutaneously, in the left or right, preferably left, pectoral region) in accordance with known techniques such as described in U.S. Pat. No. 5,292,338 to Bardy.

Electrodes used to carry out the present invention are typically carried by catheters or leads, which are electrically and mechanically connected to the housing through a header unit, and which are insertable into the heart (typically through the superior or inferior vena cava) without the need for surgical incision into the heart, in accordance with known techniques. The term "catheter" as used herein includes "stylet" and is also used interchangeably with the term "lead".

An electrode positioned "through the coronary sinus ostium and within a vein on the surface of the left ventricle of the heart", as that phrase is used herein, may reside in any of a variety of locations. It may be located in:

(1) the coronary sinus itself, (2) the portion of the great cardiac vein which runs along the base plane of the heart;

(3) the portion of the great cardiac vein that extends around the heart to the point at which the great vein turns downward toward the apex of the heart;

(4) the portion of the great cardiac vein which runs between the base and apex of the heart (either including or excluding portions of (3) above);

(5) a tributary to the great cardiac vein, such as the anterior interventricular vein, the posterior cardiac vein, or the middle cardiac vein. In addition, the electrode may be configured so that it is positioned entirely within one of the foregoing sites (see, e.g., U.S. Pat. No. 5,423,865 to Bowald et al.); or may be configured so that it is positioned in two or more adjacent sites (see, e.g., U.S. Pat. Nos. 5,014,696 to Mehra et al; 5,099,838 to Bardy; 5,193,535 to Bardy; 5,690,686 to Min et al.). For example, the electrode may be positioned: (i) in the coronary sinus and the portion of the great cardiac vein which runs along the base plane of the heart; (ii) in the portion of the great cardiac vein of the heart which runs along the base plane of the heart and the portion of the great cardiac vein that extends around the heart to the point at which the great vein turns downward toward the apex of the heart; (iii) in the portion of the great cardiac vein that extends around the heart to the point at which the great vein turns downward toward the apex of the heart and the portion of the great cardiac vein which runs between the base and apex of the heart; etc. Where the electrode is a sensing electrode, configurations that position all, or a portion of, the electrode in the coronary sinus are less preferred, and configurations that position the electrode in one or more of locations 3–5 above are more preferred.

Electrodes used to carry out the present invention, including both stimulation electrodes and sensing electrodes, may be of any suitable construction. For example, the electrodes may be rigid, hollow cylindrical electrodes electrodes which are fixed by radial expansion to a blood vessel wall and through which blood may flow, or the electrodes may be solid electrodes (ie., solid with respect to blood flow) carried by a flexible lead, which lead is sufficiently rigid to maintains the desired position of the electrode in a blood vessel. Where a solid electrode is employed , blood may or may not flow around the electrode, as discussed below.

Preferably, the left ventricle electrode is positioned within a vein traversing the lateral left ventricular free wall, midway between the base and apex of the heart (the base of the heart is identified by line 30–30' in FIG. 1; and the apex of the heart is identified by number 32 in FIG. 1). In general, depending on the particular heart anatomy, the vein is thus either the posterior cardiac vein or a tributary to the inferior cardiac vein. The electrode may be a solid electrode, because, in such small diameter veins, plugging of the vessel by the electrode is not deleterious to the patient because an alternative route of blood return around the blockage will be available.

The method of sensing electrical activations in the left ventricle (LV) myocardium from an electrode positioned in a coronary vein using an implanted device as described herein presents an opportunity to collect and utilize additional information not previously known. Such information derived from sensing the electrical activity of the LV permits improved rhythm classification and further, identification and subsequent classification of the origin of premature beats that commonly occur in ICD patients.

The effectiveness of ICD therapy is predicated on the accurate and precise classification of cardiac rhythm. The ICD continuously monitors a patients intrinsic heart rhythm. When the rhythm is classified as abnormal, the device may behave differently in comparison to times when the rhythm is normal. For example, if the intrinsic activation intervals sensed in the ventricle exceed some preset limit, a pacing pulse is issued. Still further, if the activation events are sensed in rapid succession that satisfy detection criteria, antitachycardia pacing or high voltage shocks may be delivered by the device to treat the arrhythmia. However, there are some cardiac rhythms which, while abnormally fast, might not be malignant. Examples of nonmalignant tachyarrhythmias include exercise induced sinus tachycardia and supraventricular tachycardia such as atrial flutter and atrial fibrillation.

The present invention can be carried out by utilizing the temporal sequence of activation times obtained from spatially disparate sites on the heart. The relative timing among activation events allows specific detection algorithms contained in the ICD to discriminate between rhythms that require immediate therapy and those rhythms for which therapy can be safely inhibited.

Method to Improve Sensitivity and Specificity of Rhythm Classification

FIG. 1 shows a human heart 2 residing within the thorax 4. An ICD pulse generator 6 is implanted under the skin in the infraclavicular area. Three separate leads exit the ICD header 8. Lead 10 is used for sensing electrical activity in the heart muscle and for delivery of electrical therapy to the heart. Electrode 12 (right ventricle 1; RV1) at the distal tip of lead 10 is used for pacing and sensing and is normally fabricated from a platinum material. Electrode coil 14 (right ventricle 2; RV2), mounted on lead 10, resides in the right ventricle 15 after implantation and provides an electrical discharge surface for delivery of high voltage shocks and for sensing electrical activity in the heart muscle. Electrode 16 (superior vena cava; SVC) also part of lead 10, serves as an electrical discharge surface for delivery of high voltage shocks and for sensing of electrical activity in the heart muscle. Lead 17 is an atrial lead for sensing and pacing in the right atrium 20. Electrode 18 (right atrium 2; RA2) is a ring electrode and electrode 19 (right atrium 1; RA1) is the pacing tip electrode of a standard atrial lead, known to those skilled in the art. Lead 22 is operatively connected to the ICD by header 8 and passes into the coronary sinus, into the cardiac vein and continues down a tributary, peripheral cononary vein such as the anterior interventricular vein, the posterior cardiac vein or the middle cardiac vein. An electrode 24 (left ventricle 2; LV2) can be used to pacing the heart and for sensing electrical activity, while electrode 26

(left ventricle 1; LV1) forms an electrical discharge surface for high voltage (>10 V) shocks.

Figure 2A:
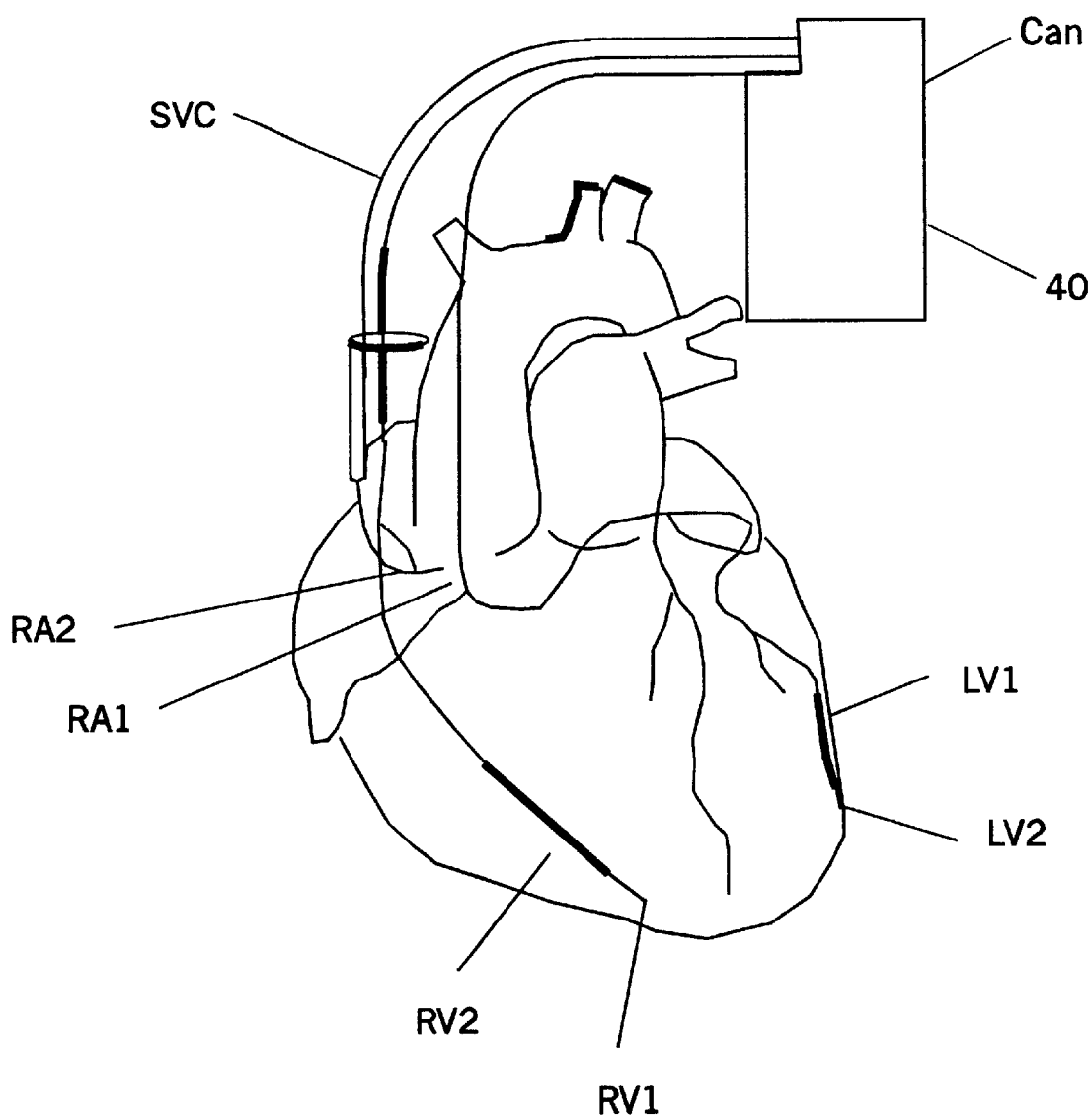
FIG. 2A illustrates an apparatus similar to that of FIG. 1.
Figure 2B:
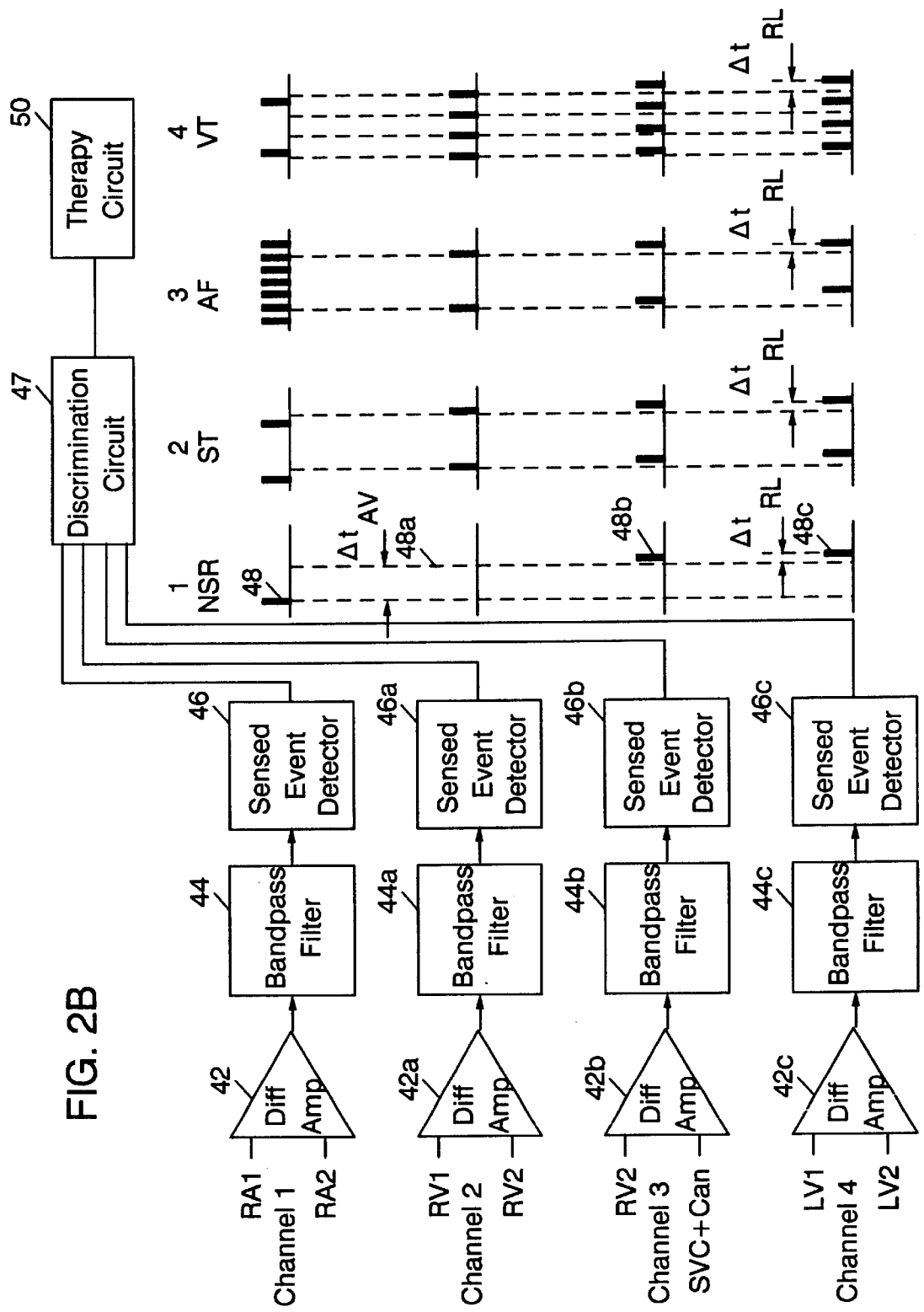
FIG. 2B illustrates the electrode connection and circuitry of an apparatus of FIG. 2A configured for detecting various types of medical conditions of the heart.

FIG. 2 shows, in panel A, an ICD 40 structurally configured essentially as described in FIG. 1. In panel B, the sensing configurations are shown. Hardware and sensed information are shown schematically, in rows, for each of channels 1 through 4. Electrograms for different electrode configurations are arranged in columns, with column illustrating normal sinus rhythm, column 2 illustrating sinus tachycardia, column 3 illustrating atrial fibrillation, and column 4 illustrating ventricular tachycardia.

Electrodes shown in the positions illustrated panel 2A are, as shown in panel 2B, operatively connected to differential amplifiers 42, 42a, 42b, 42c, in turn connected to bandpass filters 44, 44a, 44b, 44c and sensed event detector circuitry 46, 46a, 46b, 46c, contained in the ICD 40. Amplification and bandpass filtering are followed by sensed event detection. The event that is sensed by detector 46–46c is preferably the local myocardial activation time. The preferred method for determining local activation time requires computation of the first temporal derivative of the extracellular electrogram (dV/dt). The local activation time using this method corresponds to the most negative value (minimum) of dV/dt. However, the present invention is not restricted to local activation times determined solely by dV/dt criteria. Less computationally intensive methods may be utilized in implanted devices. The activation time features may include, but not be limited to a local peak in the electrogram. With reference to the preferred embodiment, the sensed event occurs when a wave of activation passes near the sensing electrode. The potential difference between the electrodes is detected by the circuitry which issues an activation time marker 48, 48a, 48b, 48c (labelled in the NSR column only).

The right panel right hand portion of panel B shows the temporal relationship among activation time markers for various rhythms, including normal sinus rhythm (NSR), sinus tachycardia (ST), atrial fibrillation (AF) and ventricular tachycardia (VT). The relative timing among the activation time markers provides a syntactic signature of the beat. During normal sinus rhythm there will exist a relationship between the activation time markers. Deviations from this normal syntactic signature may be detected by the ICD and used to discriminate among cardiac rhythms.

For normal sinus rhythm (NSR), activation time marker first appears at the atrial electrode pair (RA1 and RA2). As the wave of electrical activity passes through the sinus node and activates the RV apex, an activation time marker is registered for the RV1, RV2 recording channel. The time difference between channels 1 and 2 is $\Delta t_{AV}$ and is composed of the intra-atrial conduction time, the AV nodal delay and the intraventricular conduction time. The time difference between activation markers on channels 2 and 4 is the interventricular conduction time ($\Delta t_{RL}$), were RL means right to left. Under normal conditions, the relative timing among these sensed events remains relatively unchanged. In the presence of abnormal rhythms, this temporal sequence of events will be altered compared to NSR.

Sinus tachycardia (ST) is a cardiac rhythm often associated with physical exertion. In the absence of AV nodal conduction abnormalities, the atrial activation intervals are equal to the ventricular activation intervals, although the absolute interval in the case of ST may be only 50% of the intervals observed during NSR. The present invention contemplates that the temporal relationships between sensed events will be very similar to those that exist during NSR. In contrast, the temporal sequence of events that are present during AF and VT are markedly different than during NSR.

Representative examples of the temporal sequence of sensed events for four different cardiac rhythms are shown in FIG. 2, panel B. As will be seen, these events can be readily distinguished by a discrimination circuit 47 operatively associated with the sensed event detector. Appropriate therapy can then be triggered by a therapy circuit 50 in accordance with known techniques, as discussed in greater detail below.

In an alternative embodiment of the present invention, the temporal sequence of sensed events is combined with information concerning the shape (morphology) of certain electrograms.

Method to Predict Spontaneous Arrhythmia Onset

Potentially lethal ventricular arrhythmias occur when waves of electrical activity sweep across the ventricles with a characteristic frequency that is higher than normal. The abnormally frequent activation cycles prevent the heart from supplying sufficient oxygenated blood to sustain the viability of vital organ systems (brain, liver, kidneys and the heart itself). The underlying causes for this abnormal cardiac electrical activity are varied. The propagation of normal electrical waves of activity may be transiently perturbed by sudden changes in the electrophysiological behavior of heart cells in specific regions of the heart. Such perturbations are known to occur in the presence of obstructed blood supply or abnormal activation of nerves leading into the heart muscle. Further, the onset of ventricular tachyarrhythmias frequently occur in the presence of electrical impulses that are appear abnormally in locations that are not consistent with normal rhythm. Such impulses are called ectopic impulses. When these ectopic impulses begin to propagate from their site of origin prior to the onset of the next normal heart beat, they are said to be "premature." Such ectopic beats occurring earlier than expected are called "premature ventricular activations." When these premature ventricular activations result in a meaningful contractile response, they are termed premature ventricular contractions.

Localization of Premature Beat Origin

Premature beats have been linked to the initiation of atrial and ventricular tachyarrhythmias. Premature beats encounter regions of refractory tissue thereby establishing the electrophysiological conditions required for reentry, a mechanism of tachyarrhythmia. Premature beats occurring in the ventricles may arise from conducted atrial premature beats or from one or more ectopic foci residing in the ventricular muscle. Knowledge concerning the origin of premature beats increases the predictive accuracy of assessments related to the arrhythmogenicity of premature beats.

Figure 3A:
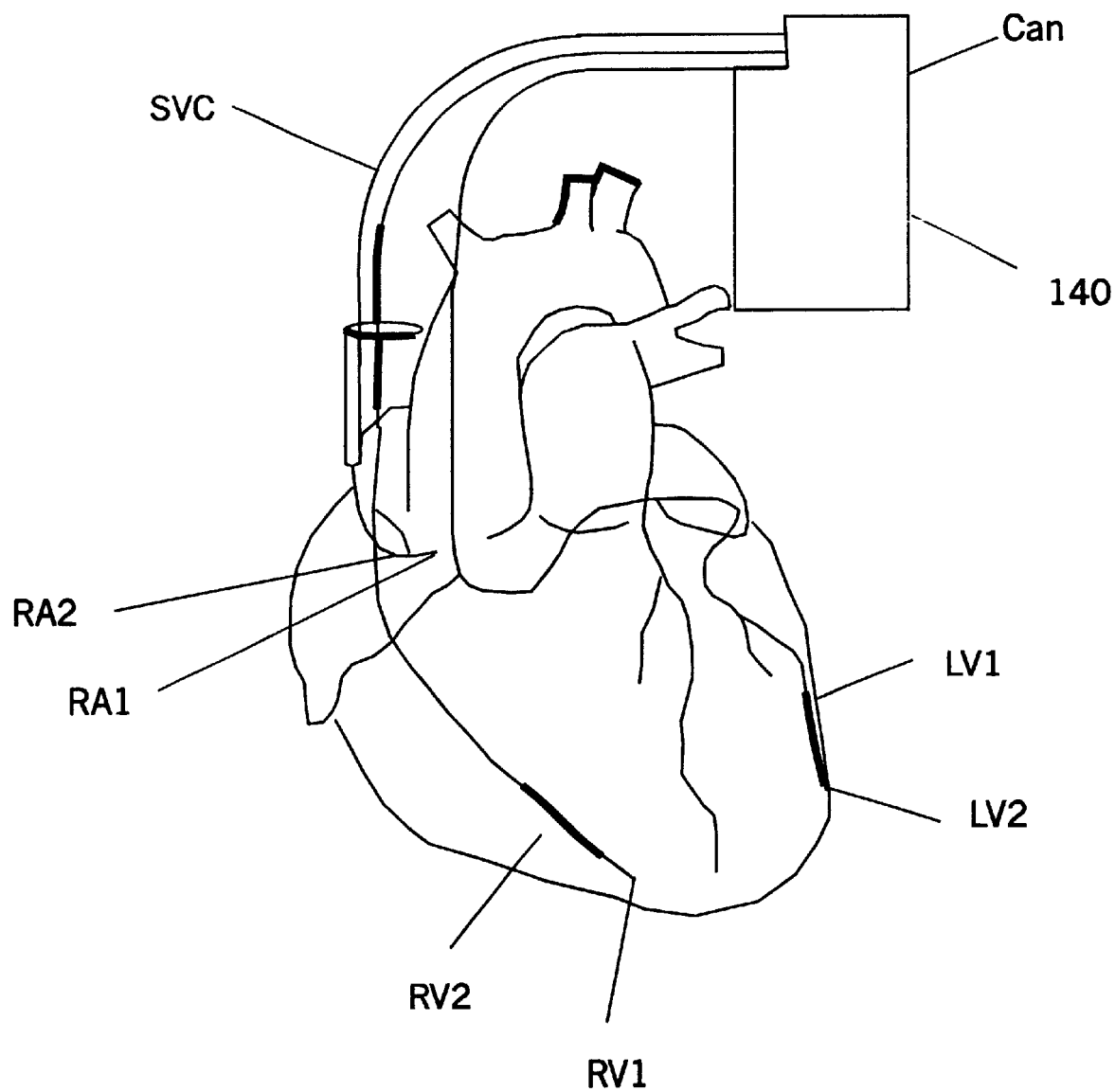
FIG. 3A illustrates an apparatus similar to that of FIG. 1.
Figure 3B:
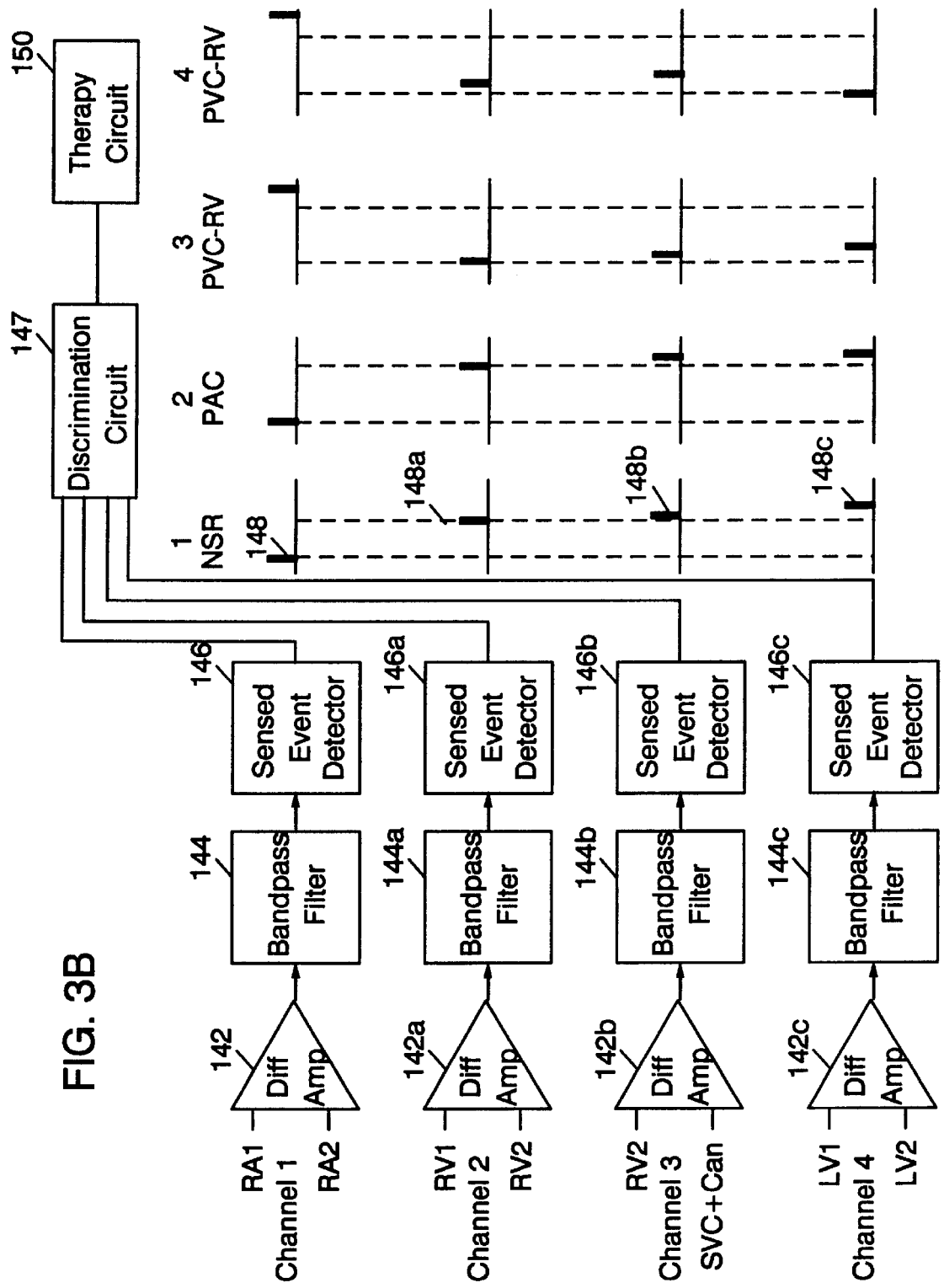
FIG. 3B illustrates the electrode connection and circuitry of an apparatus of FIG. 3A, configured for detecting premature beats and thereby predicting various medical conditions of the heart.

FIG. 3 is essentially the same as FIG. 2, except that it illustrates how an apparatus of the present invention can be employed so that the temporal sequence of sensed events permits determination of the origin of the premature beat. Panel 3A, shows an ICD 140 structurally configured essentially as described in FIG. 1. In panel 3B, the sensing configurations are shown. Hardware and sensed information are shown schematically, in rows, for each of channels 1 through 4. Electrograms for the different electrode configurations are arranged in columns, with column 1 illustrating normal sinus rhythm, column 2 illustrating premature atrial contraction (PAC), column 3 illustrating right ventricle premature ventricular contraction (PVC-RV), and column 4 illustrating left ventricle premature ventricular contraction (PVC-LV).

There are several benefits, not readily apparent, provided by the determination of the premature ventricular activation frequency and identification of the premature ventricular activation chamber of origin. First, the origin of premature ventricular activation is indicative of electrophysiological stability of the ventricles. Changes in the origin and frequency of ventricular premature activations thus indicates the onset of spontaneous ventricular tachyarrhythmia.

In order to predict the spontaneous onset of potentially lethal ventricular tachyarrhythmias, the electrophysiological status of the heart muscle must be monitored. A goal of this monitoring is to determine the frequency and location of premature ventricular activations (ectopic beats) and to determine the electrophysiological state of the heart in order to predict the likelihood that any one of the premature ventricular activations will yield a potentially lethal ventricular tachyarrhythmia.

The electrophysiological state of the heart can be characterized by analyzing characteristics of sensed electrical signals acquired by implanted devices containing appropriate amplifiers, filters and computational algorithms. During normal sinus rhythm an intrinsic electrical impulse spontaneously arises in the right atrium and is conducted to the ventricles through the atrio-ventricular node to the ventricles. Electrograms recorded from electrodes provide information about the conduction of the impulse and the repolarization of tissue. When the impulse traveling the heart muscle propagates near the sensing electrode, the amplitude of the signal changes, typically reaching a maximum as the impulse propagates closest to the sensing electrode. The moment at which the rate of change in the electrogram signal reaches a maximum is called the local activation time. By comparing the local activation times from several sensing electrodes located in different regions of the heart, a relationship between the activation times is established for normal heart rhythms. Each sensing site is connected to a separate sensing channel. The temporal sequence of activation times present among the various sensing channels forms; a "syntactic signature" for the normal heart rhythm. When a premature ventricular activation is detected the temporal relationship among activation times will be altered. An algorithm is applied to the sensed activation times to determine the chamber from which the premature ventricular activation originated. The frequency and chamber origin of premature ventricular activations is tabulated by the device and reported to the physician during device interrogation by the physician.

Thus, different cardiac conditions can be predicted by discrimination circuit 147, and this information either downloaded from the device, or used to trigger a therapeutic treatment from ICD 140 by activation of a therapy circuit 150 contained therein.

Therapy systems

As noted above, the present invention may, if desired, provide for treatment of the diagnosed or prognosed medical condition of the heart. In this case, the system will further include a therapy circuit 50 or 150, as illustrated in FIGS. 2 and 3 above. Any suitable therapy circuit may be employed, including but not limited to those described in U.S. Pat. Nos. 5,282,837 to Adams, 5,433,729 to Adams, 5,014,696 to Mehra, 5,099,838 to Bardy, 5,431,683 to Bowald, and 5,690,686 to Min. In general, the therapy circuit comprises a plurality of primary electrodes (for example, various pairs of electrodes 16, 14, 26, and 6 (where electrode 6 refers to an active external portion of the housing)) configured for delivering a therapeutic pulse to the heart; a power supplied (contained within the ICD); and a control circuit (contained within the ICD) operatively associated with the power supply, the primary electrodes and the predictor circuit, the control circuit configured for delivering a therapeutic pulse through the primary electrodes upon the prediction of future onset of cardiac arrhythmia in the patient. The discrimination circuit 47 or 147 as illustrated in FIGS. 2 and 3 serves as the prediction circuit. Preferably, one of the primary electrodes for the therapeutic pulse is configured for positioning through the coronary sinus ostium and within a vein on the surface of the left ventricle of the heart (e.g., electrode 26 in FIG. 1).

As used herein, "means" such as detector means may be implemented as various forms of hardware, including circuits and integrated circuits, as software, and as combinations of hardware and software.

The foregoing is illustrative of the present invention, and is not to be construed as limiting thereof. Numerous additional features can be added to the instant invention. For example, the electrophysiological status of the heart muscle can be determined for each cardiac activation cycle (beat), or may be determined intermittently, the measurement being made only during select times separated by periods during which no measurements are made. Analyses can be simultaneously done on features extracted from electrograms that relate to the conduction of an impluse and features that relate to the recovery (repolarization) of heart tissue. Features related to the conduction of an impluse may be the width of a local electrogram and absolute time differences between sensed events at spatially disparate sensing sites throughout the heart. Features related to conduction may be conduction intervals of intrinsic or paced impulses determined by computing the time difference between sensed events obtained from sensing electrodes positioned in the right atrium, the right ventricle, and in a vein on the surface of the left ventricle. The dynamical behavior of the conduction intervals may be monitored. Accordingly, the invention is defined by the following claims, with equivalents of the claims to be included therein.

What which is claimed is:

1. An implantable system for detecting electrical activity from a patient's heart, comprising:
   a first sensing electrode configured for positioning through the coronary sinus ostium and within a vein on the left surface of the left ventricle of said heart for sensing electrical activity from said heart;
   a second sensing electrode configured for positioning in the right ventricle of said heart for sensing electrical activity from said heart; and
   detector means operatively associated with said both first sensing electrode and said second sensing electrode for diagnosing or prognosing a medical condition of said heart with both said sensed electrical activity;
   wherein said detector means detects premature beats in said heart for said diagnosis or prognosis of said medical condition of said heart with both said sensed electrical activity.

2. An implantable system according to claim 1, further comprising a third sensing electrode configured for positioning in the right atrium or superior vena cava of said heart;
   wherein said detector means is operatively associated with all of said first, second, and third sensing electrodes;
   and wherein said detector means is configured to diagnose or prognose a medical condition of said heart by relating information obtained from said first, second, and third electrodes.

3. An implantable system according to claim 1, wherein said detector means identifies the heart chamber of premature beat origin in said heart.

4. An implantable system according to claim 1, wherein said detector means detects the presence of sinus rhythm with syntactic relationships among electrogram features for said diagnosis or prognosis of said medical condition of said heart with said sensed electrical activity.

5. An implantable system according to claim 1, wherein said detector means predicts cardiac arrhythmia in said patient prior to the onset of said cardiac arrhythmia for said diagnosis or prognosis of said medical condition of said heart with said sensed electrical activity.

6. An implantable system according to claim 1, wherein said detector means discriminates the location of origin of premature beats in said heart for for said diagnosis or prognosis of said medical condition of said heart with said sensed electrical activity.

7. An implantable system according to claim 6, wherein said detector means predicts future onset of cardiac arrhythmia from said sensed electrical activity; said system further comprising:
   a plurality of primary electrodes configured for delivering a therapeutic pulse to said heart;
   a power supply; and
   control circuit means operatively associated with said power supply, said primary electrodes and said detector means for delivering a therapeutic pulse through said primary electrodes upon the prediction of future onset of cardiac arrhythmia in said patient by said detector means.

8. An implantable system according to claim 7, wherein a first one of said primary electrodes is configured for positioning through the coronary sinus ostium and within a vein on the surface of the left ventricle of said heart.

9. An implantable system according to claim 1, wherein said detector means includes a determining circuit configured to determine the presence of cardiac arrhythmia a in said patient.

10. An implantable system according to claim 9, further comprising:
   a plurality of primary electrodes configured for delivering a therapeutic pulse to said heart;
   a power supply; and
   a control circuit operatively associated with said power supply, said primary electrodes and said determining circuit, said control circuit configured for delivering a therapeutic pulse through said primary electrodes upon the determination of the presence of cardiac arrhythmia in said patient.

11. An implantable system according to claim 9, wherein a first one of said primary electrodes is configured for positioning through the coronary sinus ostium and within a vein on the surface of the left ventricle of said heart.

12. An implantable system for detecting electrical activity from a patient's heart, comprising:
   a first sensing electrode configured for positioning through the coronary sinus ostium and within a vein on the left surface of the left ventricle of said heart for sensing electrical activity from said heart;
   a second sensing electrode configured for positioning in the right ventricle of said heart for sensing electrical activity from said heart; and
   detector means operatively associated with said both first sensing electrode and said second sensing electrode for diagnosing or prognosing a medical condition of said heart with both said sensed electrical activity;
   wherein said detector means predicts cardiac arrhythmia in said patient prior to the onset of said cardiac arrhythmia for said diagnosis or prognosis of said medical condition of said heart with both said sensed electrical activity.

13. An implantable system according to claim 12, further comprising a third sensing electrode configured for positioning in the right atrium or superior vena cava of said heart;
   wherein said detector means is operatively associated with all of said first, second, and third sensing electrodes;
   and wherein said detector means is configured to diagnose or prognose a medical condition of said heart by relating information obtained from said first, second, and third electrodes.

14. An implantable system according to claim 12, wherein said detector means detects the presence of sinus rhythm with syntactic relationships among electrogram features for said diagnosis or prognosis of said medical condition of said heart with said sensed electrical activity.

15. An implantable system according to claim 12, wherein said detector means predicts future onset of cardiac arrhythmia from said sensed electrical activity; said system further comprising:
   a plurality of primary electrodes configured for delivering a th erapeutic pulse to said heart;
   a power supply; and
   control circuit means operatively associated with said power supply, said primary electrodes and said detector means for delivering a therapeutic pulse through said primary electrodes upon the prediction of future onset of cardiac arrhythmia in said patient by said detector means.

16. An implantable system according to claim 15, wherein a first one of said primary electrodes is configured for positioning through the coronary sinus ostium and within a vein on the surface of the left ventricle of said heart.

17. An implantable system according to claim 12, wherein said detector means includes a determining circuit configured to determine the presence of cardiac arrhythmia in said patient.

18. An implantable system according to claim 17, further comprising:
   a plurality of primary electrodes configured for delivering a therapeutic pulse to said heart;
   a power supply; and
   a control circuit operatively associated with said power supply, said primary electrodes and said determining circuit, said control circuit configured for delivering a therapeutic pulse through said primary electrodes upon the determination of the presence of cardiac arrhythmia in said patient.

19. An implantable system according to claim 18, wherein a first one of said primary electrodes is configured for positioning through the coronary sinus ostium and within a vein on the surface of the left ventricle of said heart.

20. An implantable system for detecting electrical activity from a patient's heart, comprising:
   a first sensing electrode configured for positioning through the coronary sinus ostium and within a vein on the left surface of the left ventricle of said heart for sensing electrical activity from said heart;
   a second sensing electrode configured for positioning in the right ventricle of said heart for sensing electrical activity from said heart; and detector means operatively associated with said both first sensing electrode and said second sensing electrode for diagnosing or prognosing a medical condition of said heart with both said sensed electrical activity;

wherein said detector means discriminates the location of origin of premature beats in said heart for said diagnosis or prognosis of said medical condition of said heart with both said sensed electrical activity.

21. An implantable system according to claim 20, further comprising a third sensing electrode configured for positioning in the right atrium or superior vena cava of said heart;

wherein said detector means is operatively associated with all of said first, second, and third sensing electrodes;

and wherein said detector means is configured to diagnose or prognose a medical condition of said heart by relating information obtained from said first, second, and third electrodes.

22. An implantable system according to claim 20, wherein said detector means detects the presence of sinus rhythm with syntactic relationships among electrogram features for said diagnosis or prognosis of said medical condition of said heart with said sensed electrical activity.

23. An implantable system according to claim 20, wherein said detector means descrimenates an atrial location of origin from a ventricular location of origin of premature beats in said heart.

24. An implantable system according to claim 20, wherein said detector means predicts future onset of cardiac arrhythmia from said sensed electrical activity; said system further comprising:

a plurality of primary electrodes configured for delivering a therapeutic pulse to said heart;

a power supply; and control circuit means operatively associated with said power supply, said primary electrodes and said detector means for delivering a therapeutic pulse through said primary electrodes upon the prediction of future onset of cardiac arrhythmia in said patient by said detector means.

25. An implantable system according to claim 24, wherein a first one of said primary electrodes is configured for positioning through the coronary sinus ostium and within a vein on the surface of the left ventricle of said heart.

26. An implantable system according to claim 20, wherein said detector means includes a determining circuit configured to determine the presence of cardiac arrhythmia in said patient.

27. An implantable system according to claim 26, further comprising:

a plurality of primary electrodes configured for delivering a therapeutic pulse to said heart;

a power supply; and a control circuit operatively associated with said power supply, said prinary electrodes and said determining circuit, said control circuit configured for delivering a therapeuticpulse through said primary electrodesupon the determination of the presence of cardiac arrhythmia in said patient.

28. An implantable system according to claim 26, wherein a first one of said primary electrodes is configured for positioning through the coronary sinus ostium and within a vein on the surface of the left ventricle of said heart.

* * * * *